United States Patent
Hayam et al.

(10) Patent No.: US 10,765,371 B2
(45) Date of Patent: Sep. 8, 2020

(54) METHOD TO PROJECT A TWO DIMENSIONAL IMAGE/PHOTO ONTO A 3D RECONSTRUCTION, SUCH AS AN EPICARDIAL VIEW OF HEART

(71) Applicants: Biosense Webster (Israel) Ltd., Yokneam (IL); Takehiro Kimura, Tokyo (JP)

(72) Inventors: Gal Hayam, Tivon (IL); Natan Sharon Katz, Atlit (IL); Takehiro Kimura, Tokyo (JP)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 799 days.

(21) Appl. No.: 15/476,097

(22) Filed: Mar. 31, 2017

(65) Prior Publication Data
US 2018/0279954 A1 Oct. 4, 2018

(51) Int. Cl.
*A61B 5/00* (2006.01)
*G16H 30/40* (2018.01)
(Continued)

(52) U.S. Cl.
CPC .......... *A61B 5/6852* (2013.01); *A61B 5/0084* (2013.01); *A61B 5/0408* (2013.01);
(Continued)

(58) Field of Classification Search
CPC ...... A61B 18/1482; A61B 2018/00351; A61B 2018/00577; A61B 2018/00642;
(Continued)

(56) References Cited

U.S. PATENT DOCUMENTS

| 5,435,310 | A | 7/1995 | Sheehan et al. |
| 6,650,927 | B1 | 11/2003 | Keidar |
| 2005/0163357 | A1 | 7/2005 | Makram-Ebeid et al. |
| 2006/0074289 | A1* | 4/2006 | Adler ..................... A61B 5/065 600/407 |

(Continued)

FOREIGN PATENT DOCUMENTS

| EP | 3056148 A1 | 8/2016 |
| WO | 2013044182 A1 | 3/2013 |

OTHER PUBLICATIONS 3D reconstruction from multiple images. (Dec. 28, 2016). Retrieved from <https://web.archive.org/web/20161228221404/https://en.wikipedia.org/wiki/3D_reconstruction_from_multiple_images>.

(Continued)

*Primary Examiner* — Amelie R Davis
(74) *Attorney, Agent, or Firm* — Volpe and Koenig, P.C.

(57) ABSTRACT

A three-dimensional (3D) electrical mapping system and method may be used to generate a 3D image of the epicardial surface of a heart by integrating one or more epicardial images with a 3D image of the cardiac structure that may be generated by real-time 3D location and mapping system for cardiac mapping and ablation. The visual textural representation of the epicardial surface of the heart may be reconstructed using, for example, an image sensor or camera-based catheter to collect images of the epicardial surface. For each image that is captured, the system and method may store the image data along with the corresponding catheter location, orientation and/or distance information relative to the cardiac structure. The location, orientation, and/or distance information may be used to reconstruct a 3D textural model of the epicardial surface of the cardiac structure.

18 Claims, 6 Drawing Sheets

(51) Int. Cl.
*G16H 50/50* (2018.01)
*A61B 5/0408* (2006.01)
*A61B 5/0464* (2006.01)
*A61B 5/06* (2006.01)
*A61B 18/14* (2006.01)
*A61B 18/00* (2006.01)

(52) U.S. Cl.
CPC ............ *A61B 5/0464* (2013.01); *A61B 5/065* (2013.01); *A61B 18/1482* (2013.01); *G16H 30/40* (2018.01); *G16H 50/50* (2018.01); *A61B 2018/00351* (2013.01); *A61B 2018/00577* (2013.01); *A61B 2018/00642* (2013.01); *A61B 2576/023* (2013.01)

(58) Field of Classification Search
CPC ............ A61B 2576/023; A61B 5/0084; A61B 5/0408; A61B 5/0464; A61B 5/065; A61B 5/6852; G16H 30/40; G16H 50/50
See application file for complete search history.

(56) References Cited

U.S. PATENT DOCUMENTS

| | | | |
|---|---|---|---|
| 2007/0055128 A1* | 3/2007 | Glossop | A61B 1/005 600/407 |
| 2007/0299352 A1 | 12/2007 | Harlev et al. | |
| 2010/0201687 A1 | 8/2010 | Breeuwer et al. | |
| 2012/0071751 A1 | 3/2012 | Sra et al. | |
| 2014/0088457 A1 | 3/2014 | Johnson | |
| 2015/0313445 A1* | 11/2015 | Davidson | A61B 1/00009 600/109 |
| 2015/0327753 A1* | 11/2015 | Amirana | A61B 90/35 600/317 |
| 2016/0128553 A1* | 5/2016 | Geng | A61B 5/0064 600/111 |

OTHER PUBLICATIONS

Cremers et al. (May 20, 2015). Computer Vision Group Multi-View 3D Reconstruction. Retrieved from <http://vision.in.tum.de/research/image-based_3d_reconstruction/multiviewreconstruction>.

* cited by examiner

US 10,765,371 B2

METHOD TO PROJECT A TWO DIMENSIONAL IMAGE/PHOTO ONTO A 3D RECONSTRUCTION, SUCH AS AN EPICARDIAL VIEW OF HEART

SUMMARY

A three-dimensional (3D) electrical mapping system and method may be used to generate a 3D image of the epicardial surface of a heart by integrating one or more epicardial images with a 3D image of the heart that may be generated by real-time 3D location and mapping system for cardiac mapping and ablation. The visual representation of the epicardial surface of the heart may be reconstructed using, for example, an image sensor or camera-based catheter to collect images of the epicardial surface including textural details. For each image that is captured, the system and method may store the image data along with the corresponding catheter location, orientation and/or distance information relative to the heart. The location, orientation, and/or distance information may be used to reconstruct a 3D textural model of the epicardial surface of the heart.

DETAILED DESCRIPTION OF THE EMBODIMENTS

Cardiac ablation is a medical procedure performed by electrophysiologists that may be used to correct heart rhythm defects, known as arrhythmias, by creating lesions to destroy tissue in the heart that contributes to the rhythm defects. An example arrhythmia that can be treated using cardiac ablation is atrial fibrillation (AF), which is an abnormal heart rhythm that originates in the atria of the heart.

Cardiac ablation may employ long, flexible catheters that may be inserted through a small incision in the groin and through the blood vessels to the heart, and may be used to apply energy (e.g., radio frequency (RF) energy, or extreme cold) to produce small scars or lesions on the tissue to block faulty electrical impulses that may cause the heart rhythm disorders. Real-time three-dimensional (3D) location and mapping technology may be employed to visualize the exact position and orientation of a catheter within the heart and act as an advanced navigation system to enable the electrophysiologist to visualize and carefully guide the catheter to administer the RF energy in the appropriate locations. Goals of cardiac ablation are to remove the arrhythmia to return the patient's heart to a normal heart rhythm or reduce the frequency of arrhythmia and the severity of symptoms in the patient.

An example of a real-time 3D location and mapping system for cardiac ablation is the CARTO® 3 System, produced by Biosense Webster®, Inc., a subsidiary of Johnson & Johnson. The CARTO® 3 System uses electromagnetic technology to create 3D maps of a patient's cardiac structure and to display the exact location and orientation of the catheters (or other objects) in the heart. The CARTO® 3 System compensates for patient and cardiac motion to ensure accurate, real-time visualization of the cardiac structures.

Figure 1:
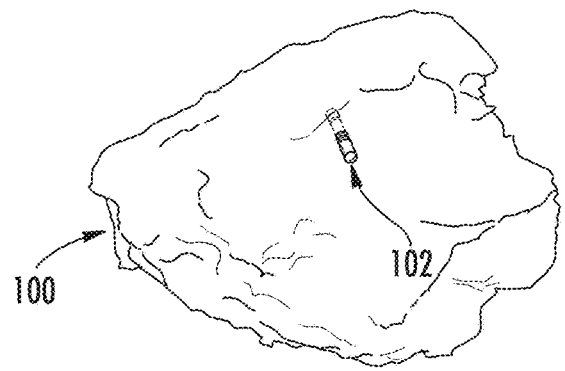
FIG. 1 shows a drawn depiction of an example three-dimensional (3D) cardiac map of a patient's heart generated by a CARTO® 3 System, in accordance with the disclosures herein.

FIG. 1 shows an example 3D cardiac map of the heart 100 of a patient generated by a CARTO® 3 System. The location and orientation of a catheter 102 is illustrated within the 3D visualization of the heart 100 of the patient. The catheter 102 may be a therapeutic and/or diagnostic catheter. Other objects and images, although not shown, may be included in the 3D visualization shown in FIG. 1 such as, but not limited to, the following: the location and orientation of additional catheters and devices; a 3D synthetic heart model used for orientation within the mapped heart 100; a two-dimensional (2D) image to assist in directional (e.g., up, down, back, forward) orientation; and fluoroscopy images or other background images.

Figure 2A:
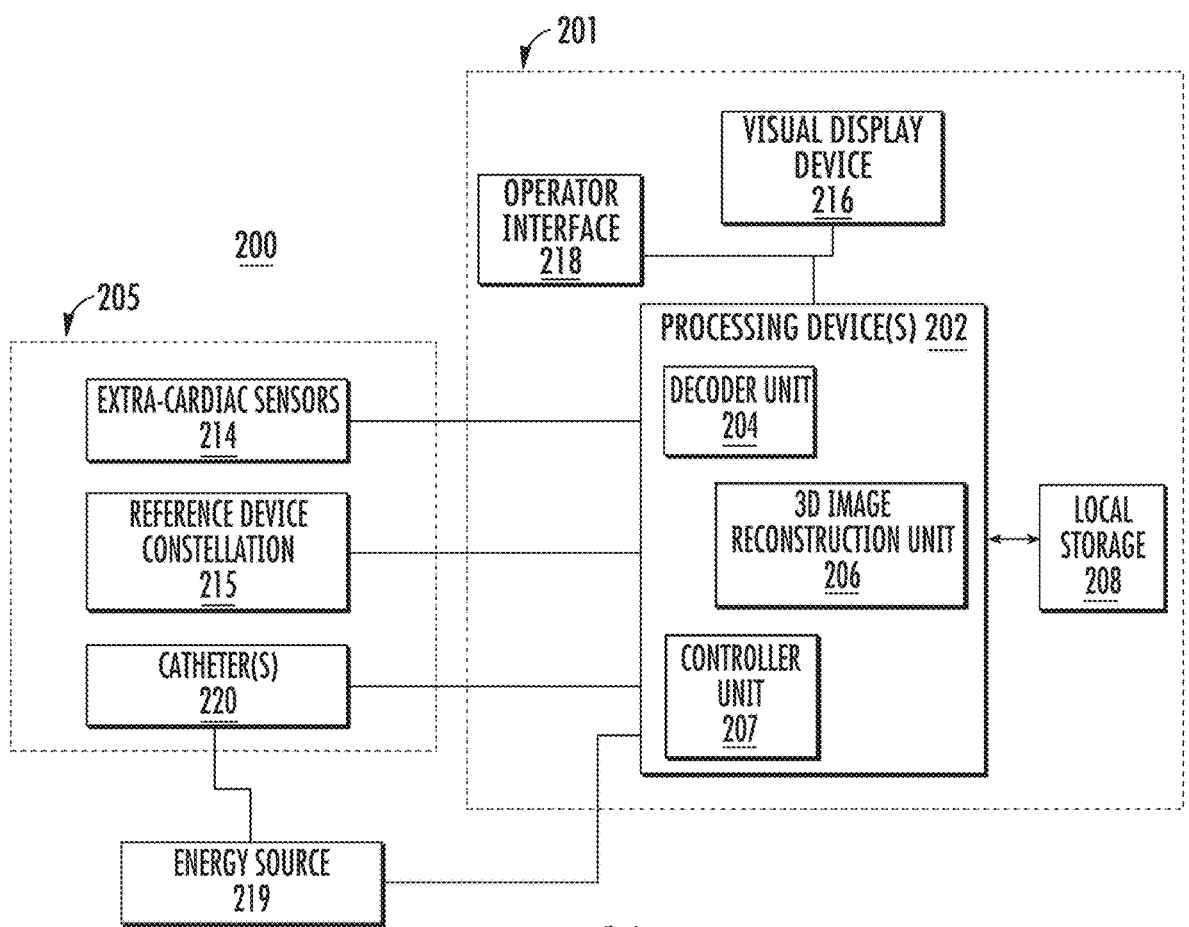
FIG. 2A is a schematic diagram of an example cardiac mapping and ablation system, in accordance with the disclosures herein.

FIG. 2A is a schematic diagram of an example cardiac mapping and ablation system 200 with integrated real-time 3D location and mapping technology (e.g., CARTO® 3 System or other 3D location and mapping technology), in accordance with the disclosures herein. The cardiac mapping and ablation system 200 may include, but is not limited to include, any of the following components: a console system 201; extra-cardiac sensors 214; reference device constellation 215; energy source 219; and/or catheter(s) 220. The console system 201 may include, but is not limited to include, any of the following components: processing device(s) 202; local storage 208; visual display device 216; and/or operator interface(s) 218. Certain elements of the cardiac mapping and ablation system 200 may be used directly on, in, and/or in proximity to the patient 205 in order to gather information to be used for visualization, diagnostics, and to perform ablation therapy. This information may be provided to the console system 201 for processing, visualization and operator control and direction, some of which is described below.

The reference device constellation 215 (e.g., may be referred to as a location pad) may include a ring of computer-controlled (e.g., controlled by processing device(s) 202) magnets positioned beneath the patient 205. The magnets may have known and fixed strength and position values that may be used as point of origin references for the magnetic fields in the surrounding space and may provide the reference information to the processing device(s) 202 to be used in producing accurate 3D images of the heart.

The extra-cardiac sensor(s) 214 may be electrodes on the skin of a patient 205, for example. The extra-cardiac sensor(s) 214 may detect electrical activity of the heart via detection of electrical changes on the skin due to the electro-physiologic pattern of the heart, and provide information on the electrical activity to the processing device(s) 202 to be used in diagnosing arrhythmias and determining a therapeutic course of action. Processed versions of the extra-cardiac signals detected by the extra-cardiac sensor(s) 214 may be displayed on visual display device 216.

One or more devices may be used on the patient 205 for therapeutic and diagnostic purposes. In the example cardiac mapping and ablation system 200, catheter(s) 220 are shown and described for these purposes; however, other devices may be used for diagnostics and/or therapeutic treatment.

One or more catheter(s) 220 may be percutaneously inserted by a physician through the patient's 205 vascular system into the heart of the patient 205. The catheter(s) 220 may be equipped with location and/or electrical sensors for the purpose of gathering information for diagnostic mapping and/or delivering therapeutic treatment (e.g., performing ablation). Different types of catheter(s) 220 may be used including, but not limited to, the following example types: fixed catheter; deflectable catheter; bi-directional catheter; uni-directional catheter; tricuspid mapping catheter; halo-shaped tip catheter; basket catheter; and/or lasso-shaped catheter. When the catheter(s) 220 is used for performing ablation on a target location (e.g., one or more locations along a path), for example by applying RF energy, the catheter(s) 220 may receive the RF energy from the energy source 219, as may be instructed by the processing device(s) 202. In an example, the catheter(s) 220 may request the RF energy directly from the energy source 219.

Figure 2B:
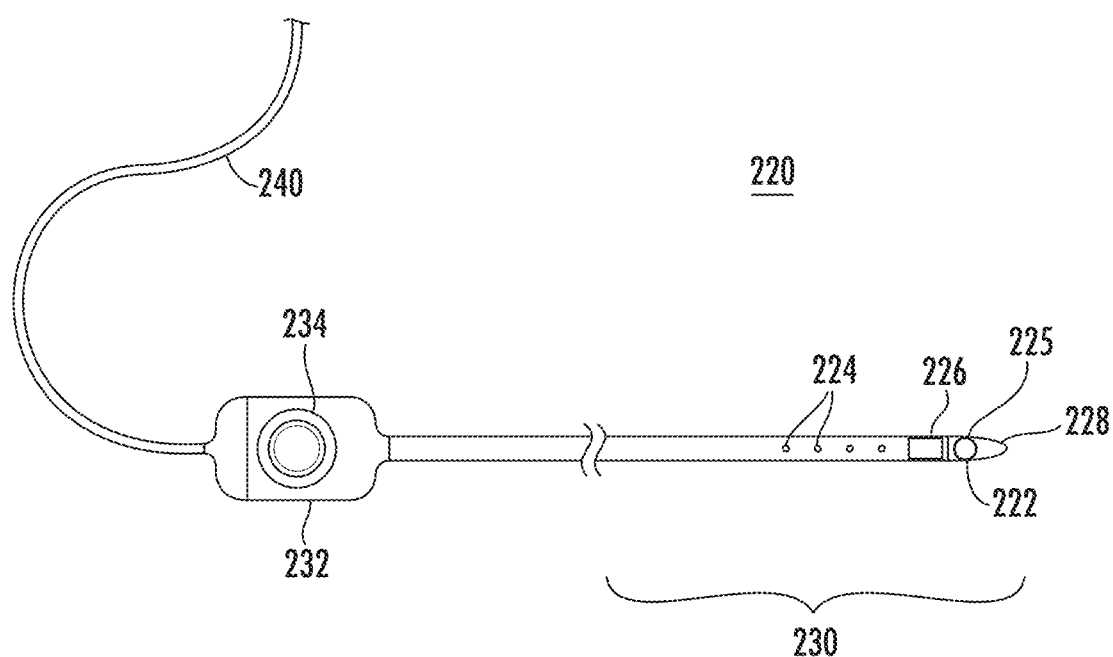
FIG. 2B is a schematic diagram of an example catheter that may be included in the example cardiac mapping and ablation system of FIG. 2A, in accordance with the disclosures herein.

An example catheter 220 is shown in greater detail in FIG. 2B, showing some, but not all, of the elements that may be included in the catheter 220. A catheter 220 may include, but is not limited to include, any one or more of the following components: electrode(s) 222; non-contact electrodes 224; image sensor(s) 225; positioning sensor(s) 226; distal tip 228; distal end 230; handle 232; and/or cable 240.

The distal end 230 of the catheter 220 may include an electrode(s) 222 at the distal tip 228 that may be used to measure electrical properties of the cardiac tissue. The electrode(s) 222 may also be used to send electrical signals to the heart for diagnostic purposes. The electrode(s) 222 may also perform ablation on defective cardiac tissue by applying energy (e.g., RF energy) directly to the cardiac tissue at the desired location of ablation.

The distal end 230 may include non-contact electrodes 224 arranged in an array, which may be used to simultaneously receive and measure far-field electrical signals from the walls of the heart chamber of the patient 205. The electrode(s) 222 and non-contact electrodes 224 provide information regarding the electrical properties of the heart to the processing device(s) 202 for processing.

The catheter(s) 220 may be equipped with one or more image sensor(s) 225, such as a charge coupled device (CCD) image sensor, and/or a camera for capturing endoscopic images when inserted in a body cavity. The image sensor(s) 225 may be located at the distal end 230.

The distal end 230 may include positioning sensor(s) 226 (also called location sensors) in the distal tip 228 of the catheter 220 that may generate signals used to determine the position and orientation (and/or distance) of the catheter 220 in the body. In an example, the relative position and orientation of the positioning sensor(s) 226, the electrode(s) 222, and the distal tip are fixed and known in order to facilitate accurate positioning information of the distal tip. For example, the position of the positioning sensor(s) 226 may be determined in part based on the relative position to known positions outside the heart (e.g., based on extra-cardiac sensors 214). The use of positioning sensor(s) 226 may provide improved location accuracy within the magnetic fields in the surrounding space and provide location information that is adaptable to patient movement because the position information of the catheter 220 is relative to the anatomy of the patient 205.

The handle 232 of the catheter 220 may be operated by the physician and may include controls 234 to enable the physician to effectively steer the distal tip 228 in the desired direction.

The electrodes 222, 224, and sensors 226 may be connected to the processing device(s) 202 via wires that may pass through handle 232 and cable 240, in order to provide electrical and position information to the console system 201, which may be used to operate and display the function of the catheter 220 within the heart in real-time.

With reference to FIG. 2A, within the console system 201, the processing device(s) 202 may include one or more signal processing circuits that may be contained inside a computer, for example. The processing device(s) 202 may be implemented in hardware and/or programmed in software to carry out the functions of the cardiac mapping and ablation system 200. This software may be downloaded to the processing device(s) 202 in electronic form, over a network, for example, and/or it may be provided on tangible media, such as magnetic or optical media or other nonvolatile memory. For example, enhancement may be made to the cardiac visualization and diagnostic capabilities of the cardiac mapping and ablation system 200 by downloading and installing software modules to the processing device(s) 202. In an example, processing device(s) 202 may comprise a general-purpose computer.

The processing device(s) 202 may receive, amplify, filter and/or digitize signals (carrying information or data) from catheter 220, including signals generated by positioning sensor(s) 226, tip electrode(s) 222 and/or non-contact electrodes 224. The signals are received and used by the processing device(s) 202 to compute the position and orientation of the catheter 220 as well as the electrical characteristics of the heart chamber. In an example, appropriate circuitry may be associated with the catheter 220 itself so that processing device(s) 202 receive signals that are already amplified, filtered and/or digitized.

The processing device(s) 202 may also be used to generate and send signals, containing information or instructions, to other elements in the cardiac mapping and ablation system 200. For example, the processing device(s) 202 may generate and send real-time 3D cardiac map information for display on the visual display device 216. In another example, the processing device(s) 202 may send/receive information to/from the local storage 208. In another example, the processing device(s) 202 may send signals to the catheter(s) 220 to apply RF energy provided by the energy source 219 to an ablation target.

As explained above, processing device(s) 202 may implement specific functions, which may be represented (e.g., illustratively or physically) as separate units within the processing device(s) 202. For example, the processing device(s) 202 may include a decoder unit 204 (e.g., implemented in hardware as a processing circuit and/or software as a software module) that may be configured to receive the position signals from the positioning sensor(s) 226 in the catheter 220, and may use the position signals to calculate position, orientation, distance, temperature and/or electrocardiogram (ECG) values for the catheter distal tip 228.

In another example, the processing device(s) 202 may include a controller unit 207 for sending instructions to other devices in the system 200. For example, the controller unit 207 may send instructions to the energy source 219 to provide RF energy to the catheter(s) 220 for ablation, and may send instructions to the catheter(s) 220 to apply the RF energy to an ablation target (e.g., one or more locations along a path).

In another example, the processing device(s) 202 may include a 3D image reconstruction unit 206 (e.g., implemented in hardware as processing circuits and/or software as a software module) that may be configured to collect image data from a medical imaging system (not shown), such as a magnetic resonance imaging (MRI) system and/or a computed tomography (CT) system, as well as image data from the catheter(s) 220 (e.g., from image sensor(s) 225 in FIG. 2B). 3D image reconstruction unit 206 may use the image data to construct a simulated surface of the patient's 205 cardiac chamber and provide it to the visual display device 216 for display, as described further below.

The processing units 204, 206 and 207 are examples, and do not comprise all the possible functions that may be implemented in processing device(s) 202. Other functionality and/or processing units may be included in processing device(s) 202 but are not shown.

Visual display device 216 may be used to display 2D and/or 3D visual representations and/or maps of the heart and show the exact location and orientation of the catheter 220 within the heart, based on information processing done in the processing device(s) 202. For example, maps may be displayed as anatomical maps, cardiac electrical activation maps, cardiac electrical propagation maps, cardiac electrical potential maps, impedance maps, cardiac chamber geometry, and ECG fragmentation maps.

In addition to the cardiac representations/maps and catheter(s), other objects in view and/or information (e.g., labels, diagnostics etc.) relevant to the mapping, diagnostic and therapeutic procedures may also be displayed on visual display device 216. The 3D visual representation of the cardiac mapping is a critical tool used by the physician to provide an accurate and real-time visual guide for performing diagnostic and therapeutic cardiac procedures, such as cardiac ablation.

The operator interface(s) 218 may be used by one or more operators to interact with and control the cardiac mapping and ablation system 200. The operator interface(s) 218 may include, but are not limited to include, the following devices: a keyboard; and/or a mouse. The operator interface(s) 218 may allow operators to access and manipulate visual information, and may provide them with the ability to tag, or label, lesions to keep track of treatment strategies for individual patients.

Operators of the cardiac mapping and ablation system 200 may include, but are not limited to include, the following: a physician (e.g., an electrophysiologist) who may, for example, control the catheter, gather and interpret diagnostics, and perform the ablation procedure; and a Clinical Application Specialist (CAS) who functions as the physician's assistant during the procedures.

Ventricular tachycardia (VT or V-tach) is a type of arrhythmia that arises from improper electrical activity in the ventricles, which are the lower pumping chambers of the heart. For example, a normal heart may beat between 60-100 beats per minute (bpm), with the atria of the heart contracting first, followed by the ventricles in a synchronized fashion. In VT, the ventricles beat at a rapid rate, for example 120-300 bpm, and are no longer coordinated with the atria. There are varying degrees of severity of VT, with more severe cases potentially leading to ventricular fibrillation or cardiac arrest.

VT may be treated using ablation treatment, for example using the tools and procedures described herein. In some cases, a physician may determine that the VT originates from an electrical circuit on the outer surface of the heart, or on the epicardium (i.e., the connective tissue and fat layer immediately surrounding the heart muscle). For VT that may occur on the epicardium, cardiac ablation may be applied to the epicardium to treat the VT. For example, a puncture into the sac (epicardium) around the heart may be made just beneath the sternum to insert a catheter (e.g., catheter 220 in FIG. 2A). The catheter may be maneuvered within the epicardium to determine whether the VT originates there. If VT is located on the epicardium, then ablation treatment may be applied to the epicardium as part of VT treatment.

Existing cardiac mapping and ablation systems lack visualization of the details and texture of the epicardial surface for diagnosing and treating heart conditions on the epicardium, such as VT. For example, knowledge of the coronary arteries, small vessels, adipose tissue, and/or scar areas on the epicardial surface may be needed to perform safe and effective ablation treatment. A large number of photos may be needed to effectively display and visually reconstruct a 3D object such as the exterior view of the heart including the details of the surface and texture of the epicardium.

According to an embodiment, a video-assisted 3D electrical mapping system may be used to generate a gross 3D image of the epicardial surface of a heart by integrating one or more 2D epicardial images with a 3D map of the cardiac structure that may be generated by real-time 3D location and mapping system for cardiac ablation (e.g. a CARTO® 3 System). The 3D visual representation of the epicardial surface of the heart may be reconstructed using, for example, an image sensor or camera-based catheter to collect a stream of images of the epicardial surface. An example of an image sensor may be a charge-coupled device (CCD) image sensor, which collects pixels stored as electrical charges in a photo-sensor array to provide high quality and high-resolution images.

For each 2D epicardial image that is captured, the system may store the image data along with the corresponding catheter location, orientation and/or distance. In an example, the catheter location, orientation and/or distance may be defined relative to external sensors (e.g., a location pad and/or reference device constellation 215 in FIG. 2A) that are also used for all images to ensure a consistent relative location, orientation and/or distance information and enable accurate stitching together or combining of multiple images of aspects of the cardiac structure. Thus, the location, orientation, and/or distance of the catheter image sensor (or camera) may be used to register and reconstruct a 3D object using the 2D photos (images) by adding photos, at the known location/orientation/distance, to the 3D map of the heart.

Figure 3A:
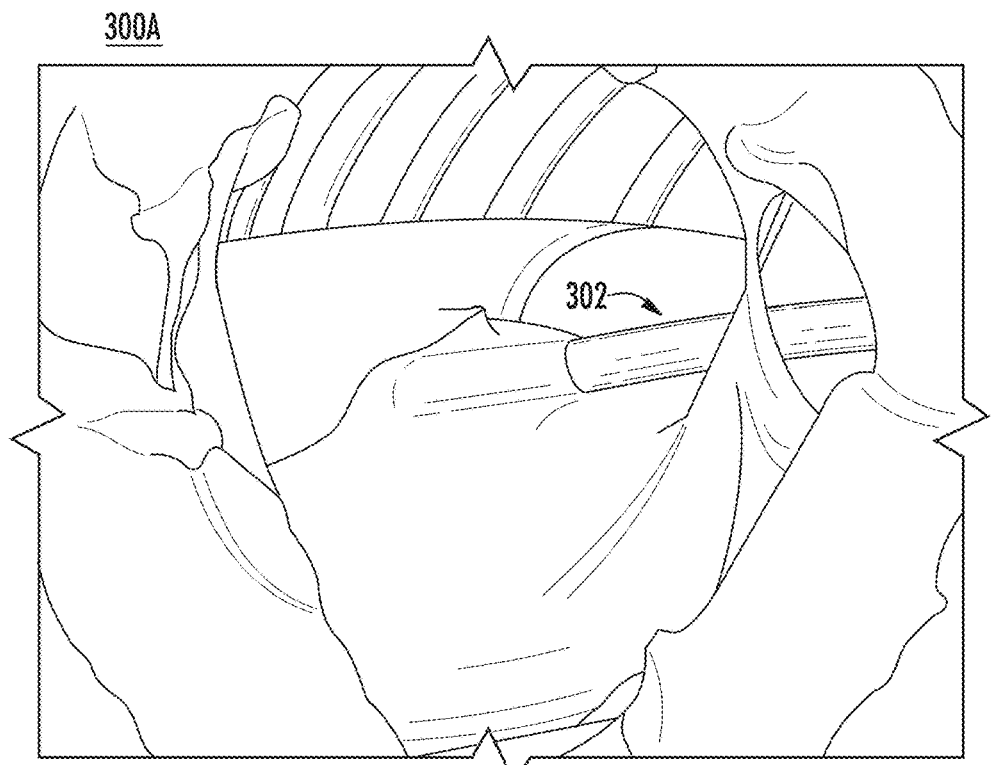
FIGS. 3A, 3B, and 3C show drawn depictions of example 2D images of a pericardial space of a cardiac structure, in accordance with the disclosures herein.
Figure 3B:
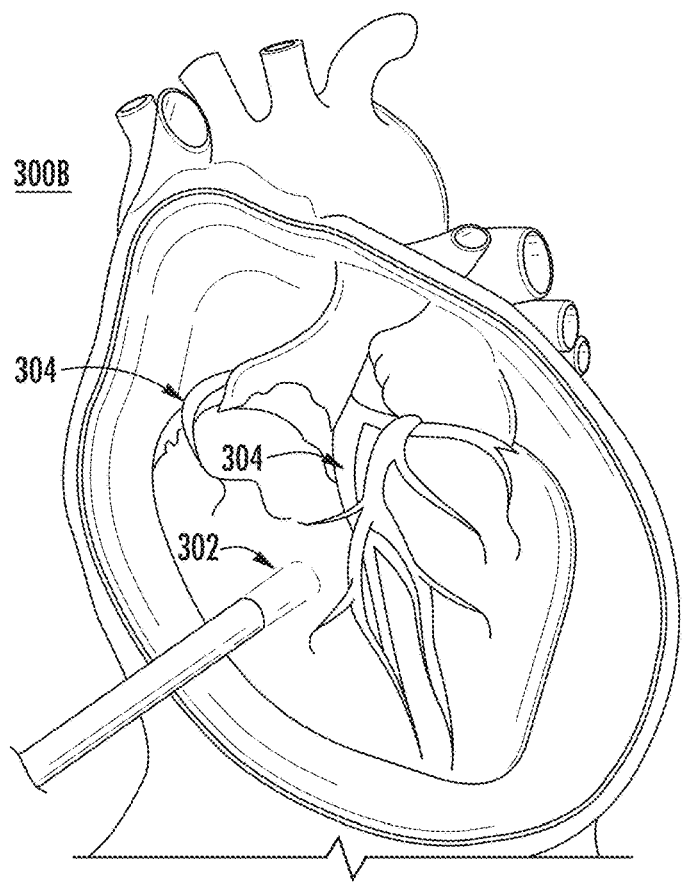
Figure 3C:
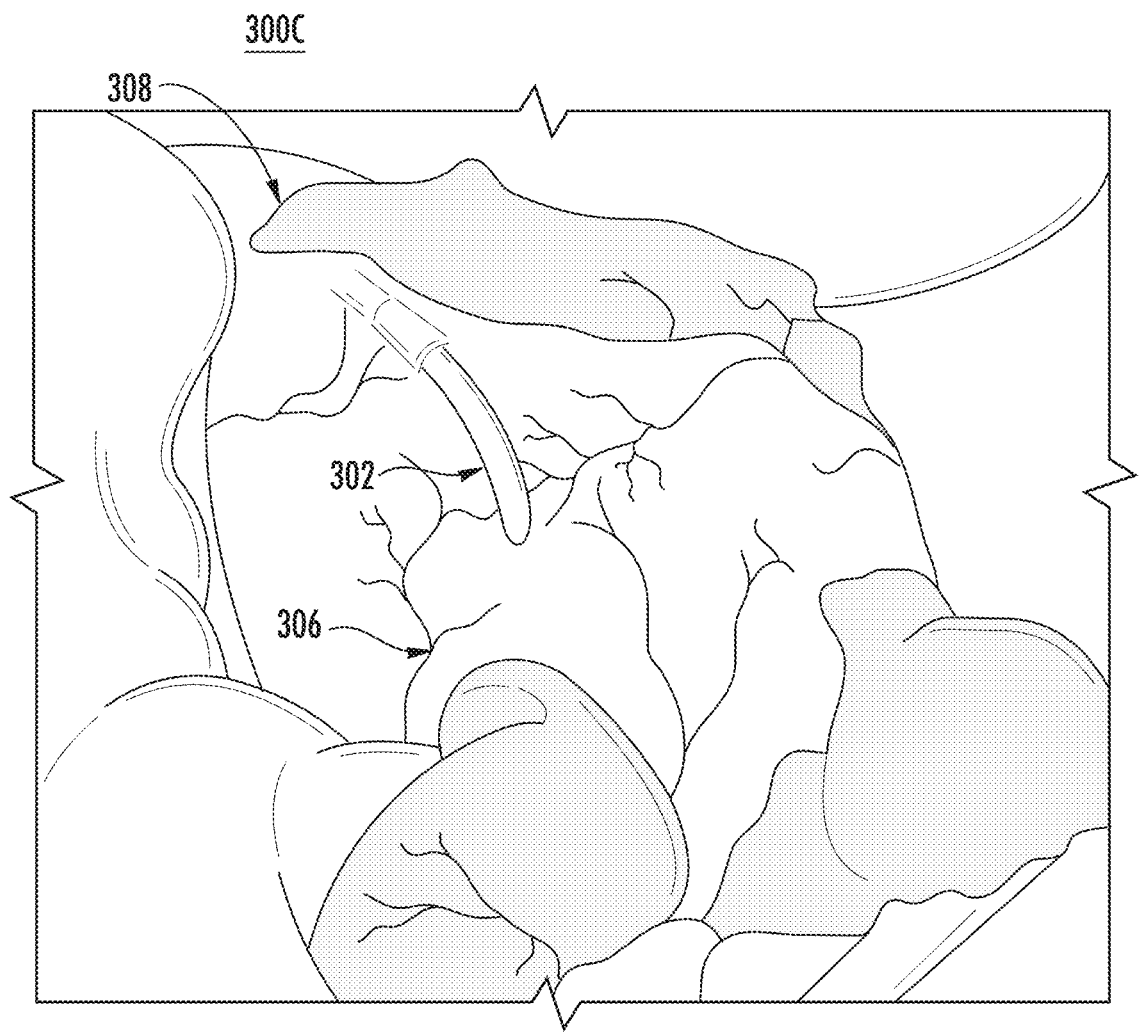

FIGS. 3A, 3B and 3C show drawn depictions of example 2D images 300A, 300B, and 300C of a pericardial space (including the epicardium) of a cardiac structure, in accordance with the disclosures herein. For example, the example 2D images 300A, 300B, and/or 300C may be captured by an image sensor mounted catheter 302 (e.g., catheter 220 in FIGS. 2A and 2B) inserted into the pericardial space through a puncture site. The example images 300A, 300B, and 300C capture textural details of the epicardial surface, including, but not limited to, the following: coronary artery 304; small vessels 306; adipose tissue 308; and/or scar lesions (not shown) (not all components of the epicardial surface are labeled or shown).

Figure 4:
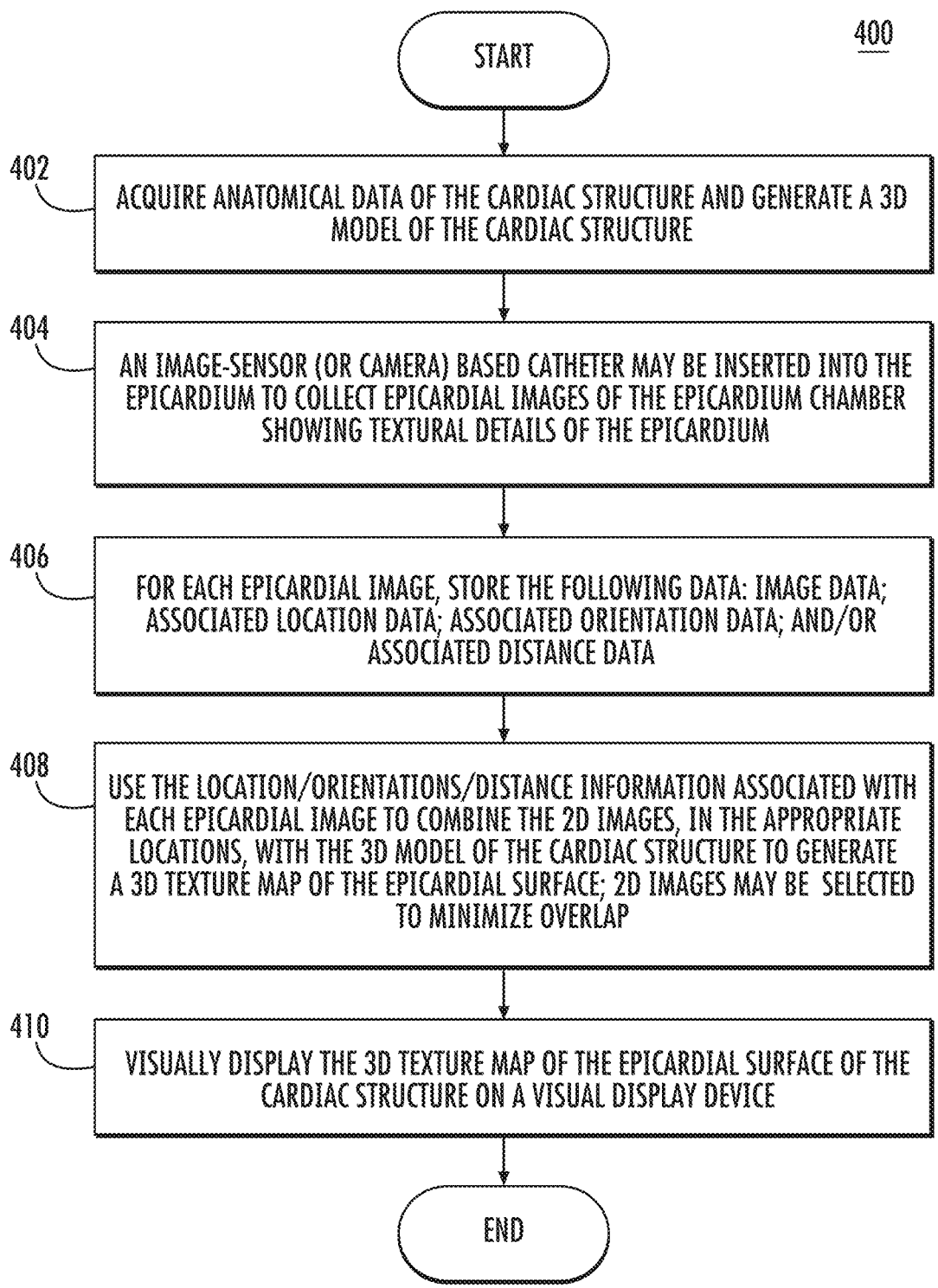
FIG. 4 is a flow diagram of an example procedure for generating a 3D textural reconstruction image of the epicardial surface of the heart, in accordance with the disclosures herein.

According to the embodiments described herein, example procedure 400 in FIG. 4 may be used to integrate multiple 2D images of the pericardial surface (e.g., images 300A-

300C in FIGS. 3A-3C) with a 3D geometric image or map of the heart (e.g., FIG. 1) to generate a 3D reconstruction image of the epicardial surface of the heart including textural details.

FIG. 4 is a flow diagram of an example procedure 400 for generating a 3D textural reconstruction image of the epicardial surface of the heart, in accordance with the disclosures herein. At 402, anatomical data of the cardiac structure may be acquired and used to generate a 3D model (or map or image) of the cardiac structure. For example, the 3D model of the cardiac structure may be generated using a real-time 3D cardiac location and mapping system such as the CARTO® 3 System. The 3D model of the cardiac structure lacks textural details of the surface of the epicardium.

To remedy the lack of detail for the epicardium, at 404, an image-sensor (or camera) based catheter may be inserted into the epicardium to collect 2D images of the epicardial surface showing textural details of the epicardium. The images may be generated, for example, using a CCD image sensor (e.g., mounted on a catheter or endoscope) and may show full details of the surface of the epicardium including, but not limited to: small vessels; coronary arteries; adipose tissue; and/or scar areas. At 406, for each epicardial image, the following data may be stored: image data; associated location data; associated orientation data; and/or associated distance data. For example, the image information collected in step 404 may be stored in storage device in a table including the location/orientation/distance information associated with each the image. For example location/orientation/distance information for a 2D epicardial image may be based on a relative position of the image-sensor mounted catheter relative to an external reference (e.g., external sensors or external location pad).

At 408, location/orientation/distance information associated with each 2D epicardial image may be used to combine the 2D images, in the appropriate locations, with the 3D model of the cardiac structure to generate a 3D texture map of the epicardial surface. For example, any algorithm for multi-view 3D reconstruction from 2D images may be used, that may involve stitching the 2D images to the 3D model at the appropriate locations using the location/orientation/distance information. In an embodiment, 2D images may be captured (during step 404) and/or selected during step 408 to minimize the amount of overlapping and redundant image information and thus reduce the number of photos required for 3D image reconstruction of the epicardium. At 410, the 3D texture map of the epicardial surface of the cardiac structure may be displayed on a visual display device (e.g., visual display device 216 in FIG. 2A) for use by a physician or operator during diagnostics and/or treatment of cardiac conditions (e.g., ablation treatment for VT).

Thus, according to the example procedure 400, the use of the location, orientation and/or distance information from the catheter may be used to map to the epicardial space images to register and construct an accurate 3D model of the heart to visualize not only the surface on the heart chamber, but also the texture of the surface of the heart chamber (epicardium). The use of the location, orientation and/or distance information from the catheter image sensor (camera) may also enable the use of fewer 2D photos of the epicardial surface by minimizing the amount of overlapping information in the photos used, and enabling the discarding of redundant photos.

Figure 5:
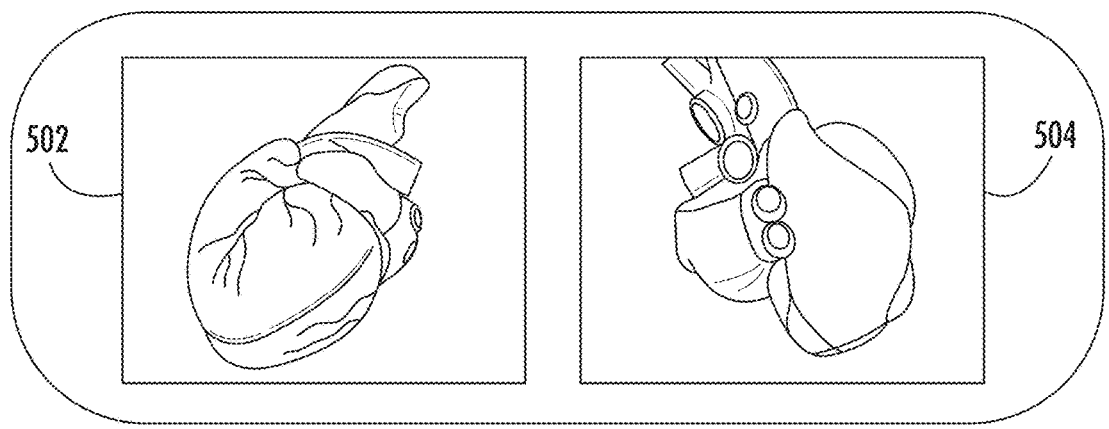
FIG. 5 shows an example high-level procedure for generating a 3D geometric reconstruction image of a non-contact 3D mapping of a cardiac structure, in accordance with the disclosures herein.
Figure 5:
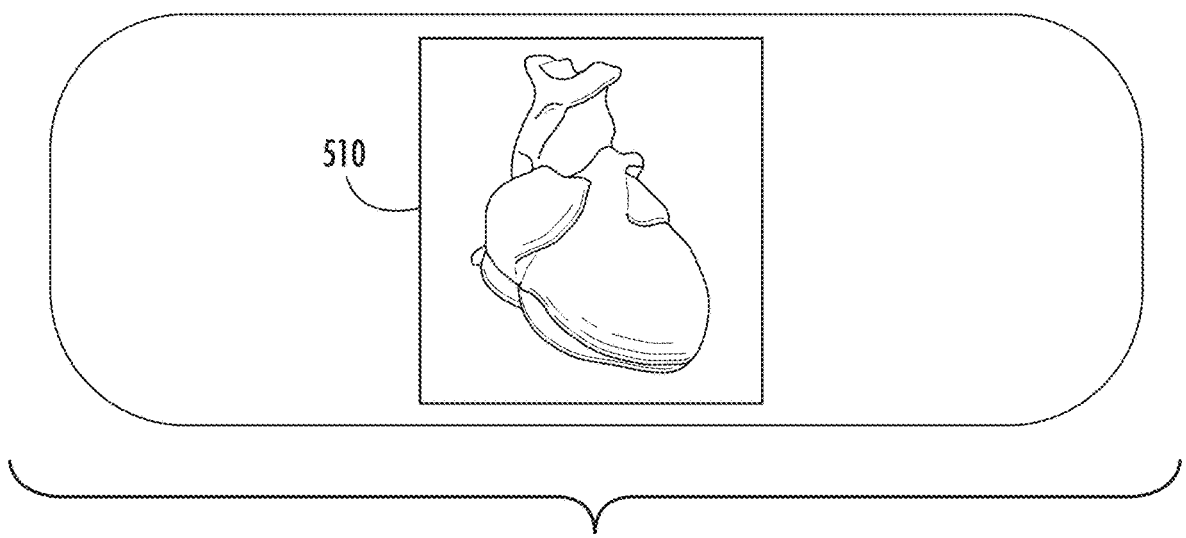

According to an example embodiment, an approach for generating a 3D reconstruction image of a cardiac structure may use a non-contact geometry construction (e.g., using non-contact sensors) and thus may provide more effective and safer ablation by providing visualization of the cardiac structure. FIG. 5 shows an example high-level procedure 500 for generating a 3D geometric reconstruction image 510 of a non-contact 3D mapping of a cardiac structure (without texture), in accordance with the disclosures herein. In the example of FIG. 5, the 2D images 502 and 504 of the cardiac structure (possibly along with other 2D images not shown) may be taken at different angles and provided to algorithm 506 to be create the 3D geometric cardiac image 510. Cardiac images 502 and 504 may be, for example, images obtained by inserting an endoscope/catheter into the cardiac structure and/or by imaging systems (MRI, CT), and algorithm 506 may be any multi-view 3D reconstruction algorithm. In an example, the procedure 500 may be used to obtain the 3D model of the cardiac structure in step 402 of procedure 400 shown in FIG. 4.

The embodiments and procedures described herein may be implemented in hardware, and/or software. A computer system for performing ablation may be capable of running software modules that introduce additional features including the procedures described herein. The procedures described herein may enable advanced cardiac visualization, and diagnostic capabilities to enhance clinicians' ability to diagnose and treat heart rhythm disorders. Although the procedures disclosed herein are describe with respect to ablation procedures within the heart, the procedures may be similarly used for ablation in other parts of the body.

It should be understood that many variations are possible based on the disclosure herein. Although features and elements are described above in particular combinations, each feature or element can be used alone without the other features and elements or in various combinations with or without other features and elements.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be mask works that are then used in a semiconductor manufacturing process to manufacture a processor which implements the methods described herein.

The methods or flow charts provided herein may be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A system configured to generate a three-dimensional (3D) texture map of an epicardial surface of a cardiac structure, the system comprising:

a processing device configured to acquire anatomical data of the cardiac structure and generate a 3D model of the cardiac structure;
a catheter configured to be inserted into an epicardium of the cardiac structure, the catheter comprising:
an image sensor configured to capture a plurality of images of the epicardial surface of the cardiac structure and provide the plurality of images to the processing device, wherein the plurality of images include textural details of the epicardial surface;
at least one location sensor configured to generate, for each of the plurality images, corresponding location, orientation and distance information and provide the corresponding location, orientation and distance information to the processing device;
the processing device further configured to generate the 3D texture map of the epicardial surface of the cardiac structure by selecting a subset of images from the plurality of images of the epicardial surface of the cardiac structure based on the corresponding location, orientation and distance information to minimize redundant information in the subset of images, and stitching the subset of images to the 3D model of the cardiac structure using the corresponding location, orientation and distance information;
the processing device configured to provide the 3D texture map of the epicardial surface of the cardiac structure to a visual display device; and
the visual display device configured to visually display the 3D texture map of the epicardial surface of the cardiac structure.

2. The system of claim 1, wherein the processing device is further configured to store the plurality of images and the corresponding location, orientation and distance information in a local storage.

3. The system of claim 1, wherein the 3D texture map of the epicardial surface of the cardiac structure shows at least one of: a coronary artery, small vessels, adipose tissue, or a scar lesion.

4. The system of claim 1, wherein the corresponding location, orientation and distance information is relative to an external reference.

5. The system of claim 1, wherein:
the processing device is configured to generate the 3D model of the cardiac structure using a multi-view 3D reconstruction algorithm.

6. The system of claim 1, wherein the image sensor is a charge-coupled device (CCD) image sensor.

7. The system of claim 1, wherein the catheter includes one or more electrodes for performing ablation on the epicardium of the cardiac structure, based on the 3D texture map of the epicardial surface of the cardiac structure.

8. The system of claim 7, wherein the one or more electrodes are configured to perform the ablation to treat ventricular tachycardia (VT).

9. The system of claim 1 further comprising:
extra-cardiac sensors configured to detect electrical activity of the cardiac structure and provide information on the electrical activity of the cardiac structure to the processing device.

10. A method for generating a three-dimensional (3D) texture map of an epicardial surface of a cardiac structure, the method comprising:
acquiring anatomical data of the cardiac structure and generating a 3D model of the cardiac structure;
capturing a plurality of images of the epicardial surface of the cardiac structure, wherein the plurality of images include textural details of the epicardial surface;
generating, for each of the plurality images, corresponding location, orientation and distance information;
generating the 3D texture map of the epicardial surface of the cardiac structure by selecting a subset of images from the plurality of images of the epicardial surface of the cardiac structure based on the corresponding location, orientation and distance information to minimize redundant information in the subset of images, and stitching the subset of images to the 3D model of the cardiac structure using the corresponding location, orientation and distance information; and
visually displaying the 3D texture map of the epicardial surface of the cardiac structure.

11. The method of claim 10, further comprising:
storing the plurality of images and the corresponding location, orientation and distance information.

12. The method of claim 10, wherein the 3D texture map of the epicardial surface of the cardiac structure shows at least one of: a coronary artery, small vessels, adipose tissue, or a scar lesion.

13. The method of claim 10, wherein the corresponding location, orientation and distance information is relative to an external reference.

14. The method of claim 10, wherein:
the generating the 3D model of the cardiac structure uses a multi-view 3D reconstruction algorithm.

15. The method of claim 10, wherein the plurality of images of the epicardial surface of the cardiac structure are captured using a charge-coupled device (CCD) image sensor mounted to a catheter inserted into an epicardium of the cardiac structure.

16. The method of claim 10, further comprising performing ablation on an epicardium of the cardiac structure based on the 3D texture map of the epicardial surface of the cardiac structure.

17. The method of claim 16, wherein the ablation is used to treat ventricular tachycardia (VT).

18. The method of claim 16, further comprising:
detecting electrical activity of the cardiac structure; and
providing information on the electrical activity of the cardiac structure for performing the ablation.

\* \* \* \* \*

UNITED STATES PATENT AND TRADEMARK OFFICE
CERTIFICATE OF CORRECTION

PATENT NO. : 10,765,371 B2
APPLICATION NO. : 15/476097
DATED : September 8, 2020
INVENTOR(S) : Gal Hayam et al.

It is certified that error appears in the above-identified patent and that said Letters Patent is hereby corrected as shown below:

On the Title Page
In Item (72), under "Inventors", in Column 1, Line 1, delete "Tivon (IL);" and insert -- Tiv'on (IL); --, therefor.

In the Specification
In Column 8, Line 9, delete "to be create" and insert -- to create --, therefor.

In the Claims
In Column 9, Line 51, in Claim 7, delete "structure7" and insert -- structure --, therefor.

Signed and Sealed this
Sixth Day of December, 2022

Katherine Kelly Vidal
*Director of the United States Patent and Trademark Office*